(12) United States Patent
Mora et al.

(10) Patent No.: US 10,111,744 B2
(45) Date of Patent: Oct. 30, 2018

(54) METHOD OF MAKING A PROSTHESIS DEVICE

(71) Applicant: Establishment Labs S.A., Alajuela (CR)

(72) Inventors: Rolando Mora, San Jose (CR); Salvador Dada, San Jose (CR); Juan Jose Chacon, San Jose (CR)

(73) Assignee: Establishment Labs S.A., La Garita, Alajuela (CR)

( * ) Notice: Subject to any disclaimer, the term of this patent is extended or adjusted under 35 U.S.C. 154(b) by 0 days.

(21) Appl. No.: 14/598,762

(22) Filed: Jan. 16, 2015

(65) Prior Publication Data

US 2015/0150675 A1 Jun. 4, 2015

Related U.S. Application Data

(63) Continuation of application No. 13/412,221, filed on Mar. 5, 2012, now abandoned.

(60) Provisional application No. 61/449,931, filed on Mar. 7, 2011.

(51) Int. Cl.
*B29C 41/02* (2006.01)
*A61F 2/12* (2006.01)
*B29C 41/22* (2006.01)

(52) U.S. Cl.
CPC ............... *A61F 2/12* (2013.01); *B29C 41/02* (2013.01); *B29C 41/22* (2013.01); *A61F 2240/001* (2013.01)

(58) Field of Classification Search
None
See application file for complete search history.

(56) References Cited

U.S. PATENT DOCUMENTS

| 3,366,975 | A | * | 2/1968 | Pangman | A61F 2/12 128/DIG. 21 |
|---|---|---|---|---|---|
| 4,455,691 | A | * | 6/1984 | Van Aken Redinger | A61F 2/12 428/447 |
| 4,650,487 | A | * | 3/1987 | Chaglassian | A61F 2/12 623/8 |
| 4,773,909 | A | * | 9/1988 | Chaglassian | A61F 2/12 623/7 |
| 5,630,844 | A | * | 5/1997 | Dogan | A61F 2/12 427/2.24 |
| 6,187,233 | B1 | * | 2/2001 | Smith | B29C 45/14778 156/230 |
| 2005/0044609 | A1 | * | 3/2005 | Vistins | B32B 27/30 2/159 |

(Continued)

*Primary Examiner* — Edmund H Lee
(74) *Attorney, Agent, or Firm* — Bookoff McAndrews, PLLC

(57) ABSTRACT

An implantable soft tissue prosthesis device comprising a silicone elastomer-shell filled with silicone gel or liquid, which among the layers that constitute its shell includes a barrier layer formed of a low permeability silicone, which impedes the bleeding or diffusion of the silicone gel from the inside of the implant to its surroundings through the shell. This barrier layer is given a coloration different to the other layers of the shell, making it visible in the finished product. The coloration of the barrier layer gives the fabricator of the implant as well as to medical personnel, the possibility to identify the presence of the barrier layer and its homogeneity, improving the safety of the device.

13 Claims, 2 Drawing Sheets

(56) References Cited

U.S. PATENT DOCUMENTS

2009/0162533 A1\* 6/2009 Kirby ................. C23C 30/00
 427/8
2009/0236771 A1\* 9/2009 Mitchell ............. F01D 5/282
 264/271.1

\* cited by examiner

METHOD OF MAKING A PROSTHESIS DEVICE

CROSS-REFERENCE TO RELATED APPLICATIONS

This application is a continuation of application Ser. No. 13/412,221, filed Mar. 5, 2012, which claims priority to U.S. Provisional Patent Application No. 61/449,931, filed Mar. 7, 2011. The entire disclosure each of these prior applications is incorporated herein by reference.

BACKGROUND OF THE INVENTION

This invention relates to an implantable prosthesis, comprising a multilayer molded elastomer shell, from which one or more of the layers are made of an elastomer with different chemical or physical properties, and which is afterwards filled with a liquid or a gel. Particularly, this invention relates to a prosthesis in which the differentiated layers are made visible by means of fabricating them with a different color material, so the differentiated layers can be easily identified in the final product by mere observation, providing a greater degree of safety of the device.

Today, the augmentation and reconstruction of the human breast requiring the use of an implant, as well as the use of soft tissue implants in other parts of the human body, have become a fairly common practice in the craft of plastic and reconstructive surgery. Typical long-term implantable devices, which are often selected for these procedures, include round, anatomical or molded silicone gel filled shapes. In recent years, the implants used for these procedures have raised concern with respect to the possibility of silicone gel bleeding through the implant shell after the implantation procedure. This concern was addressed in the prior art by the inclusion of a low diffusion barrier layer that would impede or diminish the bleeding or diffusion of the low molecular silicone particles of the silicone filler through the shell.

Conventional silicone implant shells are multilayered. Specifically, such shells include several layers and one or more inner barrier layers which are able to substantially resist gel bleeding, usually sandwiched between the outer and inner layers, but which may be located in any position in the shell structure. Some of the silicone filled breast implants include a low diffusion silicone elastomer shell made with layers of a dimethyl-diphenyl silicone elastomer, having a diphenyl polymer mole percentage of around 5%, and a barrier layer of dimethyl-diphenyl silicone elastomer having a diphenyl polymer mole percentage of around 15%. Fluor and other chemistries are also used as low diffusion silicone elastomer layers.

U.S. Pat. No. 4,455,691 discloses a gel-filled breast implant including a layered silicone elastomer shell made with outer layers of a dimethyl silicone elastomer and an intermediate barrier layer made of the reaction product of polydimethylsiloxane and either 3,3,3-trifluoropropylpolysiloxane, diphenylpolysiloxane or methylphenylpolysiloxane.

European Patent EP0030838 describes a silicone gel-filled silicone rubber article which is a flexible silicone rubber container filled with a silicone gel composition that includes an essentially continuous barrier layer of a fluorine-containing organopolysiloxane located between the container wall and the silicone gel composition to reduce the tendency of unreacted components present in the silicone gel to exude or bleed to the surface of the article.

Even though the performance of such barrier layers is considered acceptable at their present state of development, a serious problem persists in the use of this devices, both at the manufacturing and operating room levels, which is the impossibility for quality control personnel and medical staff of easily identifying the presence of the important low diffusion barrier layers within the complete prosthesis, without the use of impractical specialized equipment or without the use of destructive tests.

The same situation exists for many soft tissue implants where the same general fabrication technics are employed, i.e. breast, calf, gluteus, penile, testicular, nasal implants, and tissue expanders.

BRIEF SUMMARY OF THE INVENTION

The present invention provides an implantable device consisting of a flexible elastomer shell enclosing an internal lumen, which is filled with a liquid or gel. The shell includes multiple layers of an elastomer of which the innermost layer comes in direct contact with the filler. One or more of the layers included in the shell structure are made with a different material that will substantially impede the diffusion or bleeding of the filling material particles through the implant shell. These layers are given an identifiable coloration in order to differentiate them from the other layers. The coloration of the barrier layers allows a series of advantages over traditional implants, including the possibility of visually identifying the existence of the barrier layer in each implant, as well as the correct and homogenous application of the same. This also allows the possibility of including the control of the barrier layer as a simpler part of the quality control process in the fabrication of the implants, and allows the medical professionals who have the responsibility of employing such implants in surgical procedures to verify the presence and correctness of the barrier layer by simple observation.

BRIEF DESCRIPTION OF THE SEVERAL VIEWS OF THE DRAWINGS

Certain characteristics and advantages of the present invention may be more clearly understood with reference to the following description in conjunction with the accompanying drawings of which.

Figure 1:
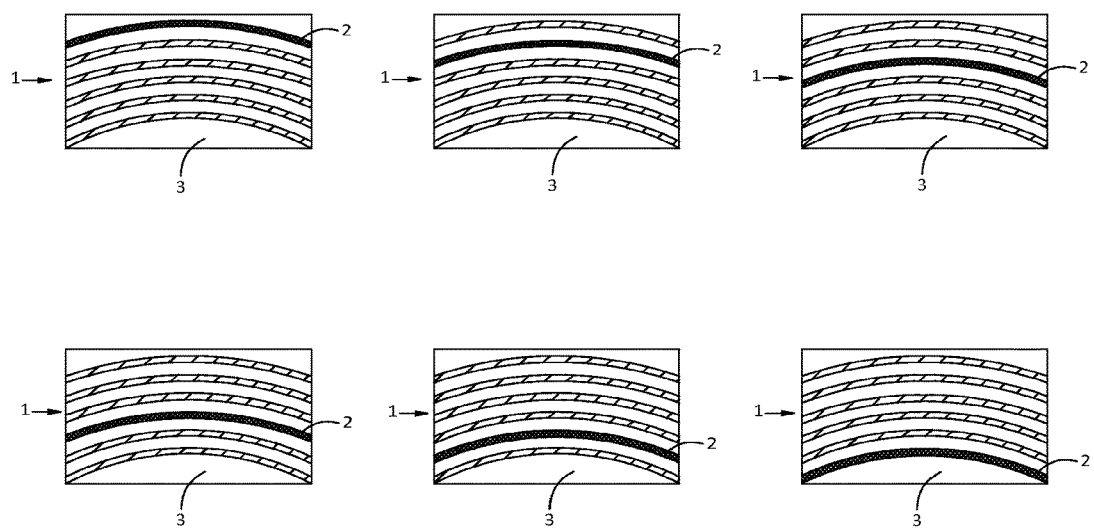
FIG. 1. Incorporates six possible examples of cross-sectional views through portions of implants of the present invention, having a multilayer shell 1 and a colored barrier layer 2 which can be found at any position of the shell, either on top, bottom or nestled between the other layers. The lumen 3 shall be occupied by the corresponding filler material.
Figure 2:
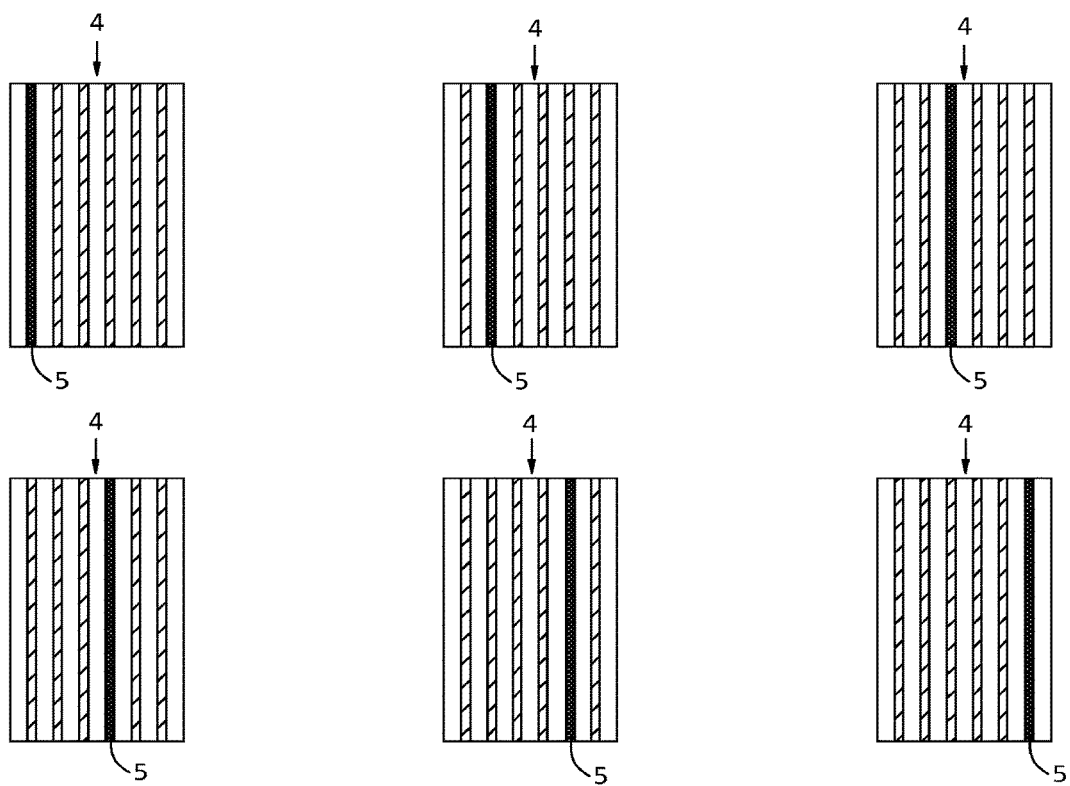
FIG. 2. Incorporates six possible examples of vertical cross-sectional views through portions of the implant shells of the present invention, having a multilayer shell 4 and one colored barrier layer 5 which can be found at any position of the shell, either on top, bottom or nestled between the other layers.

It is important to note that the number of layers included in the drawings is just an example, since the shell structure in an implant may consist of any number of layers, of which the low diffusion barrier layers incorporating the coloration may be one or more and located anywhere in the structure.

DETAILED DESCRIPTION OF THE INVENTION

The present invention provides a gel or liquid-filled implant, typically consisting of an internal silicone gel and a flexible elastomer shell enclosing the gel. The shell includes multiple layers of a silicone elastomer of which the innermost layer comes in direct contact with the filling. The multilayer shell structure includes one or more low diffusion barrier layers from which at least one shall have a color different to the other layers. The present invention is based on the fact that the low diffusion barrier layers present in the flexible shells of silicone implantable devices currently available in the market are colorless. Consequently, it is not possible for the health professionals to unequivocally establish its presence, integrity and/or uniformity during the product examination at the operating room. It is also very difficult for quality control personnel to identify these same characteristics on assembled implants during the fabrication process.

More specifically, the shell is defined as a multilayer structure in which a colored low diffusion barrier layer is either nestled between, or laid on top or below the standard elastomer layers. The barrier layer is usually a silicone elastomer comprising a polysiloxane backbone and having a minimum mole percentage of 10% of a substituted or pendant chemical group that retards permeation of silicone through the layer. The silicone elastomer usually present in the low diffusion barrier layer is a polydimethylsiloxane and the pendant chemical group is one of a phenyl or fluorine group, for example, a diphenyl group or a methylphenyl group, a trifluorpropyl group, and mixtures thereof.

Usually, the shell itself as well as the individual layers, both the colored barrier and the standard ones, have a uniform thickness. The total thickness usually ranges from about 0.33 mm to about 1.00 mm, but may vary upwards or downwards from these figures.

Advantageously, the use of a barrier layer on the implant manufacturing promotes the reduction of gel bleeding through the shell; in most cases the diphenyl or fluorine group are located in the middle of the multilayer shell. In currently available implants the diphenyl layer is uncolored, just as the dimethyl layers. This makes impossible to distinguish the presence of this important barrier layer in the finished product.

Process wise, in the manufacturing of the implants now on the market, there may be in-process controls to verify the presence of the barrier layer using an optical comparator. This control is established because it is feasible that an operator may forget to apply the barrier layer to a shell; if one implant is assembled without the barrier layer, it will be almost impossible for the surgeons to determine whether the prosthesis to be implanted has the low diffusion barrier layer or not.

Usefully, this invention allows to visually confirm the presence and homogeneity of the bleed resistant layer around the implant, which is almost invisible in the implants currently in the market.

The surgeon with this invention can unequivocally confirm the presence of a low diffusion layer by means of the visual aid.

The step of forming a colored dispersion to manufacture the colored low diffusion barrier layer may consist of adding pigments dispersed in a vinyldimethyl-terminated polydimethylsiloxane polymer. The colored dispersion shall be the dispersion containing the additional diphenyl group or fluor or any other chemistry used for gel diffusion reduction or control. The dispersion itself may be also fabricated in a material which itself may be of a different color, or a chemical agent may be added which would change the color of the material.

In a specific embodiment, the present implants are suitable for implantation in the human body and the flexible colored shell is accordingly sized and shaped.

Several systems and methods can be used for constructing a silicone implant elastomeric shell and they are contemplated in this invention. The step of forming the shell comprises coating a mold with a dispersed or liquid elastomer; the shell may be formed by dipping, spraying, pouring, blowing or rotational molding, using a suitably shaped mold, coated with dispersion of a silicone elastomer and a solvent, allowing the solvent to evaporate, and allowing the elastomer to cure, as it is contemplated and employed in the existing art.

What we claim is:

1. A method of making a prosthesis device comprising a flexible shell and a filling material, said method comprising:
    forming a plurality of first layers by coating a mold with a first silicone material, wherein the plurality of first layers has a first thickness and a first color;
    forming one or more second layers by coating the plurality of first layers with a second silicone material, comprising:
        a polydimethylsiloxane polymer having at least 10 mole percent of a pendant chemical group chosen from a diphenyl group, a methylphenyl group, a trifluoropropyl group, or a combination thereof;
        a vinyldimethyl-terminated polydimethylsiloxane polymer; and
        a pigment,
    the one or more second layers providing a diffusion barrier to impede passage of the filling material through the shell, wherein the one or more second layers has a second thickness and a second color different from the first color of the plurality of first layers;
    forming a plurality of third layers by coating the one or more second layers with the first silicone material, wherein the plurality of third layers has a third thickness greater than the second thickness and the same color as the first color of the plurality of first layers, and wherein a total thickness of the shell, comprising the first thickness, the second thickness, and the third thickness, ranges from 0.33 mm to 1.00 mm; and
    verifying the presence of the one or more second layers in the shell by visual observation of the second color in the shell, the one or more second layers being visually distinguishable through the plurality of first layers without the use of an optical comparator, specialized equipment, or destructive tests.

2. The method of claim 1, further comprising introducing the filling material into a cavity of the shell, wherein the filling material comprises a silicone gel or a silicone liquid.

3. The method of claim 1, wherein at least one of coating the mold with the first silicone material, coating the plurality of first layers with the second silicone material, or coating the one or more second layers with the first silicone material comprises dipping, spraying, pouring, blowing, or rotational molding.

4. The method of claim 1, wherein the shell has a uniform total thickness.

5. The method of claim 1, wherein the prosthesis device is a breast implant.

6. The method of claim 1, wherein the prosthesis device is suitable for implantation in a human body.

7. The method of claim 1, further comprising verifying the homogeneity of the one or more second layers in the shell by visual inspection of the second color in the shell.

8. The method of claim 1, wherein the first thickness of the plurality of first layers is greater than the second thickness of the one or more second layers.

9. The method of claim 1, wherein the step of verifying the presence of the one or more second layers in the shell by visual observation of the second color in the shell is performed in a manufacturing facility, and further comprising verifying the presence of the one or more second layers in the shell by visual observation of the second color in the shell again by a member of a medical staff.

10. A method for making a breast prosthesis, the method comprising preparing a shell by:
    coating at least a portion of a mold with a first liquid or dispersion to form a plurality of first layers having a first color, wherein the first liquid or dispersion comprises a silicone elastomer;
    coating the plurality of first layers with a second liquid or dispersion to form at least one second layer having a second color different from the first color, wherein the second liquid or dispersion comprises:
        a polydimethylsiloxane polymer having at least 10 mole percent of a pendant diphenyl group;
        a vinyldimethyl-terminated polydimethylsiloxane polymer; and
        at least one pigment;
    coating the at least one second layer with the first liquid or dispersion to form a plurality of third layers having the first color; and
    verifying the presence of the at least one second layer by visual observation of the second color through the plurality of first layers;

wherein:
    the plurality of first layers and the plurality of third layers each have a thickness greater than a thickness of the at least one second layer;
    a total thickness of the shell ranges from 0.33 mm to 1.00 mm; and
    visual observation of the second color through the plurality of first layers is performed without the use of an optical comparator, specialized equipment, or destructive tests.

11. The method of claim 10, further comprising filling the shell at least partially with a filling material in liquid or gel form, wherein the at least one second layer provides a diffusion barrier to impede passage of the filling material through the shell.

12. The method of claim 10, further comprising preparing the second liquid or dispersion before preparing the shell, wherein preparing the second liquid or dispersion comprises:
    dispersing the at least one pigment in the vinyldimethyl-terminated polydimethylsiloxane polymer to form a dispersed pigment; and
    combining the dispersed pigment with the vinyldimethyl-terminated polydimethylsiloxane polymer.

13. The method of claim 10, wherein the step of verifying the presence of the at least one second layer is performed in an operating room.

* * * * *